(12) United States Patent
Shakespeare et al.

(10) Patent No.: US 7,671,994 B2
(45) Date of Patent: Mar. 2, 2010

(54) METHOD FOR MEASURING CHEMICAL LEVELS USING PH SHIFT

(75) Inventors: Simon Adam Shakespeare, Atherstone (GB); Matthew Emmanuel Milton Storkey, Trumpington (GB)

(73) Assignee: Watkins Manufacturing Corporation, Vista, CA (US)

( * ) Notice: Subject to any disclaimer, the term of this patent is extended or adjusted under 35 U.S.C. 154(b) by 109 days.

(21) Appl. No.: 11/748,467

(22) Filed: May 14, 2007

(65) Prior Publication Data

US 2008/0285012 A1  Nov. 20, 2008

(51) Int. Cl.
*G01N 21/00* (2006.01)
(52) U.S. Cl. .............................. 356/432; 356/51; 356/36
(58) Field of Classification Search ................. 356/432, 356/51, 36
See application file for complete search history.

(56) References Cited

U.S. PATENT DOCUMENTS

| | | | |
|---|---|---|---|
| 4,448,889 A | 5/1984 | Neri et al. | |
| 4,476,095 A | 10/1984 | Scott et al. | |
| 4,657,670 A | 4/1987 | Newton | |
| 4,752,740 A | 6/1988 | Steininger | |
| 4,950,610 A * | 8/1990 | Tittle | 436/163 |
| 5,039,492 A * | 8/1991 | Saaski et al. | 422/82.09 |
| 5,104,527 A | 4/1992 | Clinkenbeard | |
| 5,155,048 A | 10/1992 | Williams et al. | |
| 5,218,304 A | 6/1993 | Kinlen et al. | |
| 5,300,442 A | 4/1994 | Frant | |
| 5,422,014 A | 6/1995 | Allen et al. | |
| 5,680,220 A | 10/1997 | Delignieres et al. | |
| 5,708,275 A | 1/1998 | Rhodes | |
| 6,093,292 A | 7/2000 | Akiyama | |
| 6,238,555 B1 | 5/2001 | Silveri et al. | |
| 6,398,961 B1 | 6/2002 | Wei et al. | |
| 6,444,129 B1 | 9/2002 | Collins | |
| 6,649,358 B1 * | 11/2003 | Parce et al. | 435/7.2 |
| 6,753,186 B2 | 6/2004 | Moskoff | |
| 7,349,760 B2 * | 3/2008 | Wei et al. | 700/267 |
| 2002/0014410 A1 | 2/2002 | Silveri et al. | |
| 2004/0154993 A1 | 8/2004 | Yanagihara et al. | |

(Continued)

FOREIGN PATENT DOCUMENTS

WO  WO 94/18543  8/1994

(Continued)

OTHER PUBLICATIONS

Written Opinion of the International Search Authority regarding PCT/US08/62385 (Counterpart of the Subject Application) - Aug. 15, 2008.

(Continued)

*Primary Examiner*—Roy Punnoose
(74) *Attorney, Agent, or Firm*—Greenberg Traurig LLP; Franklin D. Ubell

(57) ABSTRACT

A method of measuring the free chlorine level in a solution of chlorinated pool/spa water comprises a first sample of said solution having a first selected pH and a second sample of said solution having a second selected pH and determining first and second ultraviolet light (UV) transmissivity values for each of the first and second samples. The first and second transmissivity values are then used to determine the free chlorine level.

36 Claims, 13 Drawing Sheets

U.S. PATENT DOCUMENTS

| | | |
|---|---|---|
| 2005/0117150 A1 | 6/2005 | Puppels et al. |
| 2005/0276724 A1 | 12/2005 | Bremauer |
| 2006/0051874 A1 | 3/2006 | Reed et al. |

FOREIGN PATENT DOCUMENTS

| | | |
|---|---|---|
| WO | WO 95/21393 | 8/1995 |
| WO | WO 97-42497 A1 | 11/1997 |
| WO | WO 1999/028240 A1 | 6/1999 |

OTHER PUBLICATIONS

Written Opinion of the International Search Authority regarding PCT/US08/62388 - Jul. 30, 2008.

Akanbi, Isiaka O. (Examiner), Office Action Summary mailed Jan. 27, 2009, U.S. Appl. No. 11/748,461, filed May 14, 2007.

M. Ralfs et al, Disposable optochemical sensor for the determination of chlorine concentrations in the ppf-range, Sensors and Actuators B, 1997, vol. 44, pp. 257-261.

Makoto Mizoguchi et al., A Novel Method to Determine Chlorine Concentration in Tap Water Using a New Tolidine Derivative with less Cytotoxicity, Analytical Sciences, 2001, Vo. 17 Supplement, pp. i829-i831.

Watkins Manufacturing Corporation et al., Form PCT/ISA/210 in connection with PCT/US2009/034569.

Watkins Manufacturing Corporation et al., Form PCT/ISA/237 in connection with PCT/US2009/034569.

* cited by examiner

US 7,671,994 B2

METHOD FOR MEASURING CHEMICAL LEVELS USING PH SHIFT

FIELD OF INVENTION

The subject invention relates to halogen detection in fluid solutions and more particularly to a chlorine concentration detection method for analyzing chlorine concentration in spa or pool water wherein the system employs UV spectral analysis of a solution at two different pH levels.

RELATED ART

In the prior art, various devices for measuring chlorine (hypochlorous acid) concentration in water are known. Such devices include Oxidation Reduction Potential (ORP) sensors, amperometric sensors and Palin N, N-Diethyl-P-Phenylenediamine (DPD) testing apparatus.

SUMMARY

The following is a summary of various aspects and advantages realizable according to various embodiments of the invention. It is provided as an introduction to assist those skilled in the art to more rapidly assimilate the detailed discussion which ensues and does not and is not intended in any way to limit the scope of the claims which are appended hereto in order to particularly point out the invention.

According to various embodiments, a method for measuring the free chlorine level in a solution of chlorinated pool/spa water is provided wherein a pH adjusting device produces a first sample of the solution having a first selected pH and a second sample of the solution having a second selected pH. A spectral analyzer then determines first and second ultraviolet light (UV) transmissivity values for each of said first and second solution samples. The results of spectral analysis may then be supplied to an electronic processor for determining the free chlorine level using the first and second transmissivity values.

In one embodiment, the pH adjusting device may comprise first and second cell solutions, each having a respective electrode positioned therein. A switching mechanism may then be employed to switch the polarity of a voltage applied to the electrodes such that a voltage of a first polarity is applied to a first of the successive samples and a voltage of a second polarity is applied to a second of the successive samples, thereby developing samples having two different pH values.

In another embodiment, the pH adjusting device may comprise a single coaxial cell including first and second coaxial fluid flow chambers and a pair of electrodes. Successive solution samples are supplied to the cell and their pH appropriately altered.

BRIEF DESCRIPTION OF THE DRAWINGS

The above-mentioned features and objects of the present disclosure will become more apparent with reference to the following description taken in conjunction with the accompanying drawings wherein like reference numerals denote like elements and in which.

DETAILED DESCRIPTION

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, electrical, functional, and other changes may be made without departing from the scope of the present invention. The following detailed description is, therefore, not to be taken in a limiting sense, and the scope of the present invention is defined only by the appended claims. As used in the present disclosure, the term "or" shall be understood to be defined as a logical disjunction and shall not indicate an exclusive disjunction unless expressly indicated as such or notated as "xor."

The methods of the present disclosure relate to chemical, particularly halogen, detection in fluid solutions and may be particularly adapted for use in pools and spas, but also in potable water solutions and other similar applications wherein halogens are added. As chlorine is a common additive to pool and spa water, the present disclosure is described using chlorine as an exemplary chemical. Bromine, iodine, and the other halogens are expressly contemplated for use in the present system. Indeed, the apparatuses and methods of the present disclosure are applicable to nearly any chemical in solution, which allows determination of the concentration of the chemical. Artisans will recognize the modifications, such as absorption wavelength appropriate on a case by case basis without undue experimentation.

Figure 1:
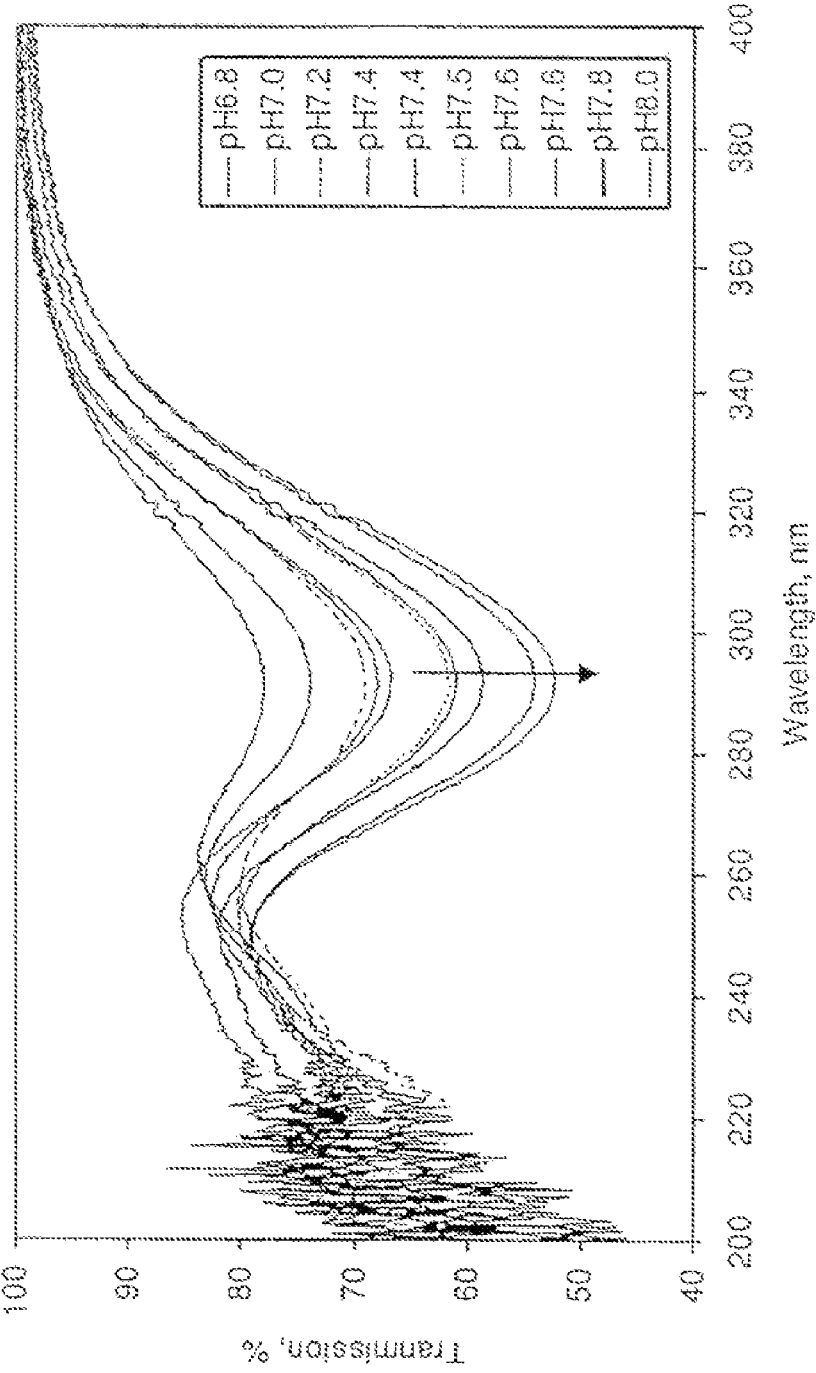
FIG. 1 is a graphical illustration of an embodiment of a percentage of ultraviolet light transmitted through a water solution containing the chlorous ion at various pH levels at a temperature of 23 degrees centigrade at a concentration of chlorine of 3 parts per million.

FIG. 1 illustrates a graph of the percentage of ultraviolet (UV) light transmitted through a water solution containing the chlorous ion ($OCl^-$) for various pH levels at a temperature of 23 degrees centigrade and a concentration of free chlorine of 3 parts per million (ppm). From FIG. 1, it may be seen that the UV transmission percentage changes as the pH shifts, e.g. at the wavelength of 293 nanometers (nm). Other wavelengths of electromagnetic radiation may also be employed depending on the chemical being measured and a useful or optimal absorption characteristic of particular chemical. For example, wavelengths in the infrared or visible spectrum are expressly contemplated.

Figure 2:
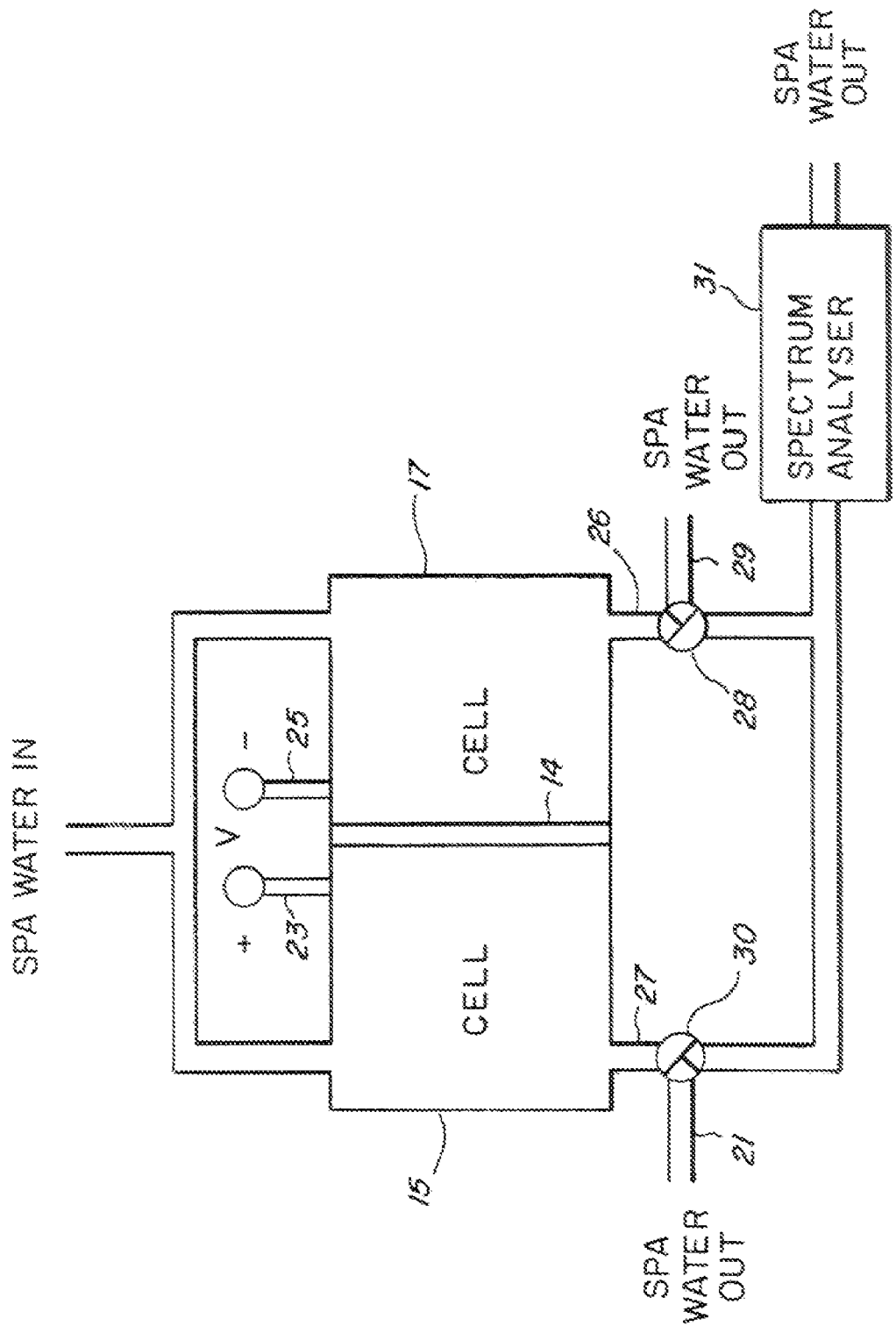
FIG. 2 is a block diagram of an embodiment of the chlorine measurement system of the present disclosure.

A chlorine measurement system which takes advantage of the pH shift phenomenon illustrated in connection with FIG. 1 is shown in FIG. 2. First cell and second cell 15, 17 respectively, both electrochemical half-cells are provided, each containing a respective half-cell solution. Each half-cell solution may comprise, for example, a sample of chlorinated pool or spa water containing hydrochlorous acid and the chlorous ion ($HOCl/OCl^-$).

The two half-cell solutions are separated by separator 14, e.g. by a salt-bridge or a semi-permeable membrane or permeable membrane. A positive electrode 23 is placed in the half-cell solution in first cell 15, while a negative electrode 25 is placed in the half-cell solution in second cell 17. In operation, negative and positive voltages are applied to the positive electrode 23 and the negative electrode 25, respectively. Application of these voltages causes acidity of the half-cell solution of the first cell 15 to increase, while acidity of the half-cell solution of the second cell 17 decreases.

To compare the respective transmission percentages of the respective solutions in the first cell 15 and second cell 17, respective samples are supplied in succession to an analyzer 31. For example, a first sample from the first cell 15 may be supplied via a conduit 27 through a "T" valve 30 to the analyzer 31. After analysis of that first sample, a second sample is provided from the second cell 17 via a conduit 26 through a "T" valve 28 to the analyzer 31. According to embodiments, the analyzer 31 is a spectrum analyzer and determines the respective transmission percentages at a selected frequency, for example, 293 nm, and then uses the respective transmission percentages to calculate the level of the $OCl^-$ ion. Using such a differential measurement technique has the advantage that other contaminants in the solution whose UV absorption does not change with pH will have no effect on the resulting $OCl^-$ measurement and therefore will not skew that measurement.

To determine the chlorine level from the difference measurement, a table may be provided that comprises the spectral difference corresponding to each of a range of chlorous ion levels at a selected wavelength. Such a table may be created by measuring the spectral difference of a range of samples, each of whose chlorous ion level is known, for example.

In operation of the system of FIG. 2, when one cell 15, 17 has its half-cell solution directed to the analyzer 31, the other cell's 17, 15 half-cell solution must be directed back to its source, for example a spa or a pool. Both cells 15, 17 need to have flowing half-cell solutions for the system to operate as intended. Bypass return conduits 21, 29 provide an outlet to the source of the half cell solution that bypasses analyzer 31. For example, when "T" valve 30 is open and directing half-cell solution of first cell 15 to analyzer 31, then "T" valve 28 is open to direct the half-cell solution of second cell 17 back to the source of the solution through bypass conduit 29. Otherwise, a build up of reactants will occur in the static solution, causing a build up of acid or base and excessive breakdown of HOCl.

Figure 3:
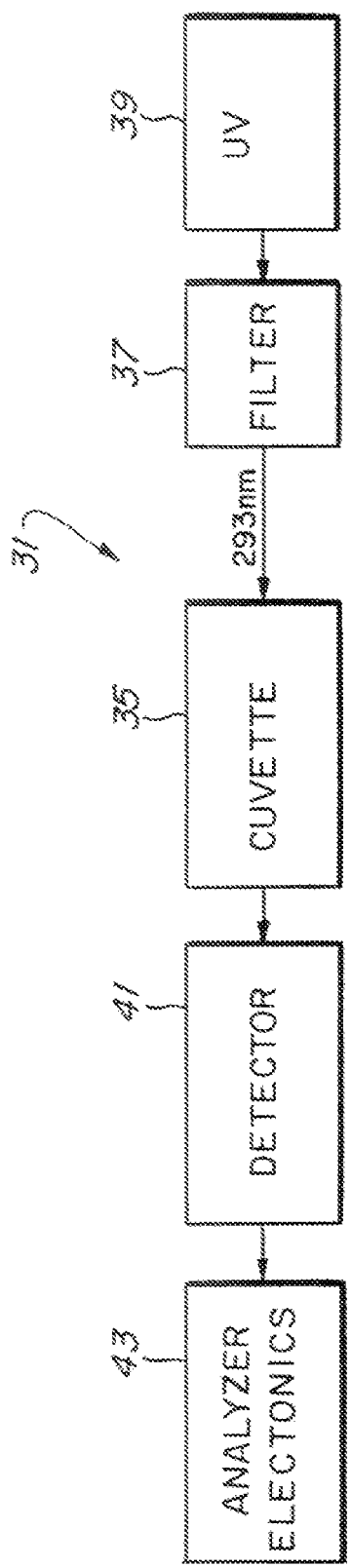
FIG. 3 is a block diagram of an embodiment of a spectrum analyzer that may be used to measure a percentage of ultraviolet light transmitted through water according to the present disclosure.

FIG. 3 depicts an illustrative analyser 31. The analyzer 31 includes a UV source 39, a filter 37, a cuvette 35, a detector 41, and analysis electronics 43. The UV source 39 and filter 37 combination provide a 293 nm wavelength, which passes through the solution sample contained in cuvette 35 to the detector 41, which may be a conventional UV detector, according to embodiments. The output of the detector 41 is applied to analysis electronics 43, which performs analog to digital (A-D) conversion and digital comparison or subtraction of the respective transmission readouts from first cell 15 and second cell 17. The analysis electronics 43 then perform a table look-up operation to determine the chlorous ion level. Analysis electronics 43 may comprise a suitable A-D converter and a microcontroller and/or computer.

Figure 4:
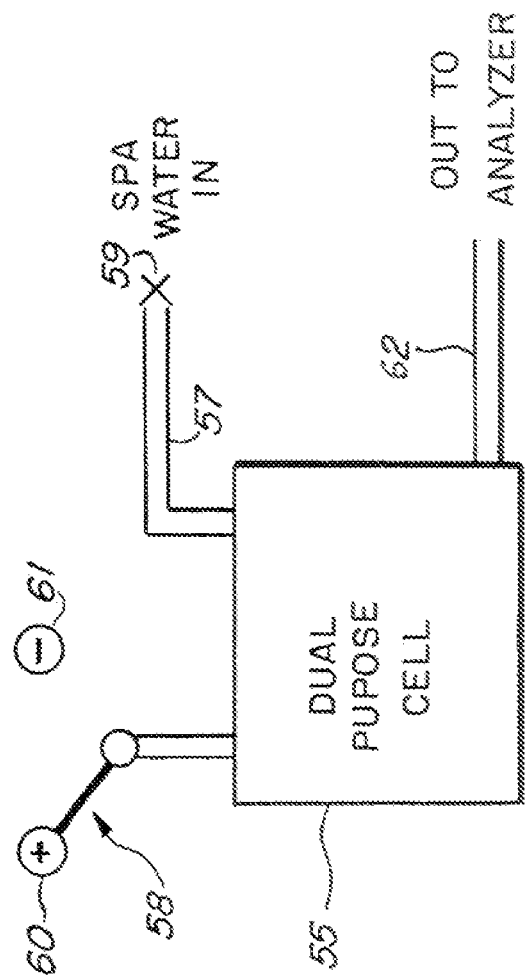
FIG. 4 is a block diagram of an embodiment of the chorine measurement system of the present disclosure.

FIG. 4 illustrates an alternative embodiment wherein single cell 55 is used rather than the dual cell embodiment of FIG. 2. In this embodiment, a first sample of half-cell solution is subjected to a positive charge and then analyzed. Thereafter, a second sample of half-cell solution is exposed to a negative charge and that sample is then passed to the analyzer 31 through outlet conduit 62. A switch 58 is depicted as being used to switch between a positive electrode 60 and a negative electrode 61. A valve 59 is shown to indicate the switching of successive half-cell solution samples into the dual-purpose cell 55 through inlet conduit 57.

Figure 5:
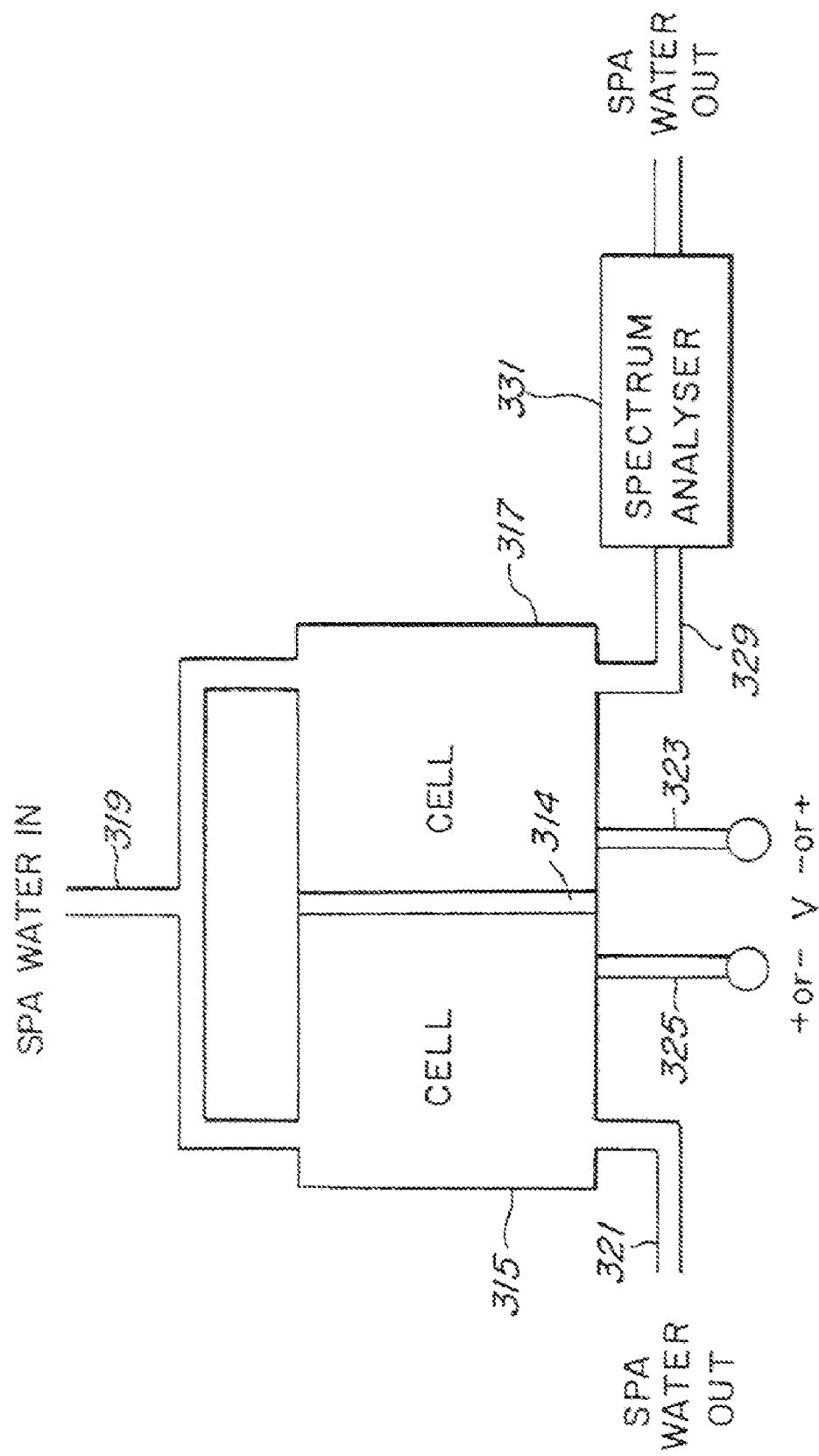
FIG. 5 is a block diagram of an embodiment of the chlorine measurement system of the present disclosure.

FIG. 5 shows a more detailed implementation of an embodiment similar to FIG. 4. As in FIG. 2, first cell 315 and second cell 317 are separated by a separator 314. Half-cell solution is supplied via a conduit 319 to first cell 315 and second cell 317 and exits via a conduit 321. A switchable voltage source V 323, 325 is arranged to apply a voltage of a first polarity to a first half-cell solution sample. A sample of the first-half-cell solution at a first pH value in the second cell 317 is then supplied to an analyzer 331 for analysis via conduit 329. Thereafter, the first half-cell solution sample is discharged via the conduit 321, and a second half-cell solution sample is loaded into first cell 315 and second cell 317 via the conduit 319. The polarity of the voltage source V is then reversed to develop a second half-cell solution sample having a second pH value for supply to the analyzer 331.

It may be observed that too much charge per unit mass can cause the pH at the negative electrode 61 to increase beyond 8.2-8.3, which leads to a highly absorbing spectra solution. Too high a voltage and drive current will therefore cause $HOCl/OCl^-$ to be electrolyzed and lost from the solution and also will cause chlorine to be emitted as well as oxygen.

Figure 6:
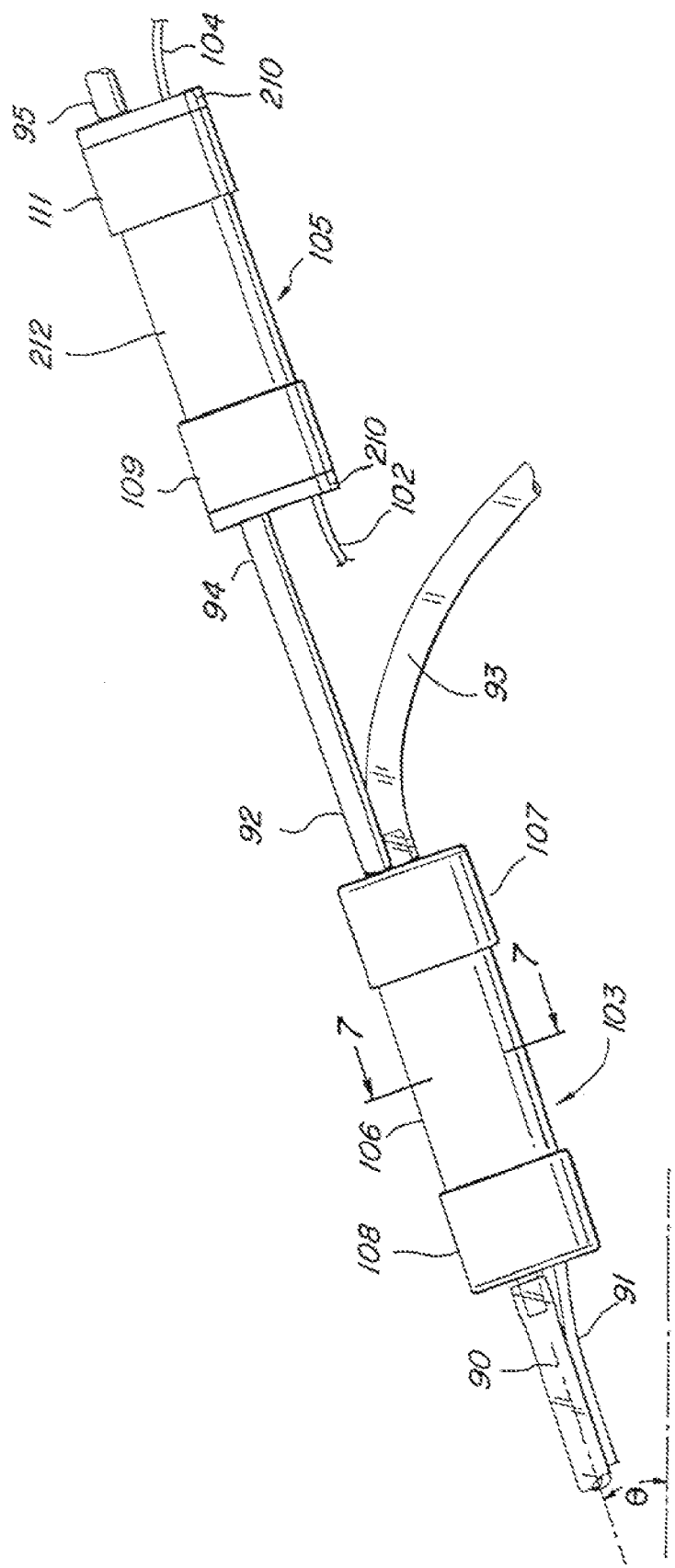
FIG. 6 is a perspective view of an embodiment of an integrated electrolysis cell and optical cell.

FIG. 6 illustrates a co-axial embodiment of an electrolysis cell 103 and an optical cell 105. The co-axial electrolysis cell 103 is disposed below the optical cell 105 and both are disposed at an acute angle θ, to the horizontal. The angle θ may be, for example, between 10° and 80°, to allow gas bubbles to be flushed out of an exit port 95.

The electrolysis cell 103 includes a central cylindrical tube 106 having first and electrolysis cell input and output end caps 108, 107, at each of its respective ends. Tubing 90 from a high pressure side is connected to the single inline port of die electrolysis cell input end cap 108. The tubing 90 may be, for example, clear PVC tubing. In the embodiment of FIG. 6, pH modulation is obtained by controlling the voltage on an electrode supply cable 91.

The electrolysis cell output end cap 107 has two outputs, 92, 93. The output 93 may be, for example, clear PVC tubing, which returns half-cell solution to the source. The second output 92 may comprise black PVC tubing extending from the outermost outlet of the end cap 108. The second output 92 is supplied to the input entry inlet 94 of the optical cell 105.

The optical cell 105 comprises a central cylindrical tube 212, onto which are mounted respective end caps 109 and 111. An end plate 210 is attached to each end cap 109, 111. The lower end cap 210 receives a UV source cable 102, while the upper end cap 210 receives a UV sensor cable 104. An exit port 95 is positioned on the topside of the optical cell 105. The cylindrical tube 212 is hollow.

Figure 7:
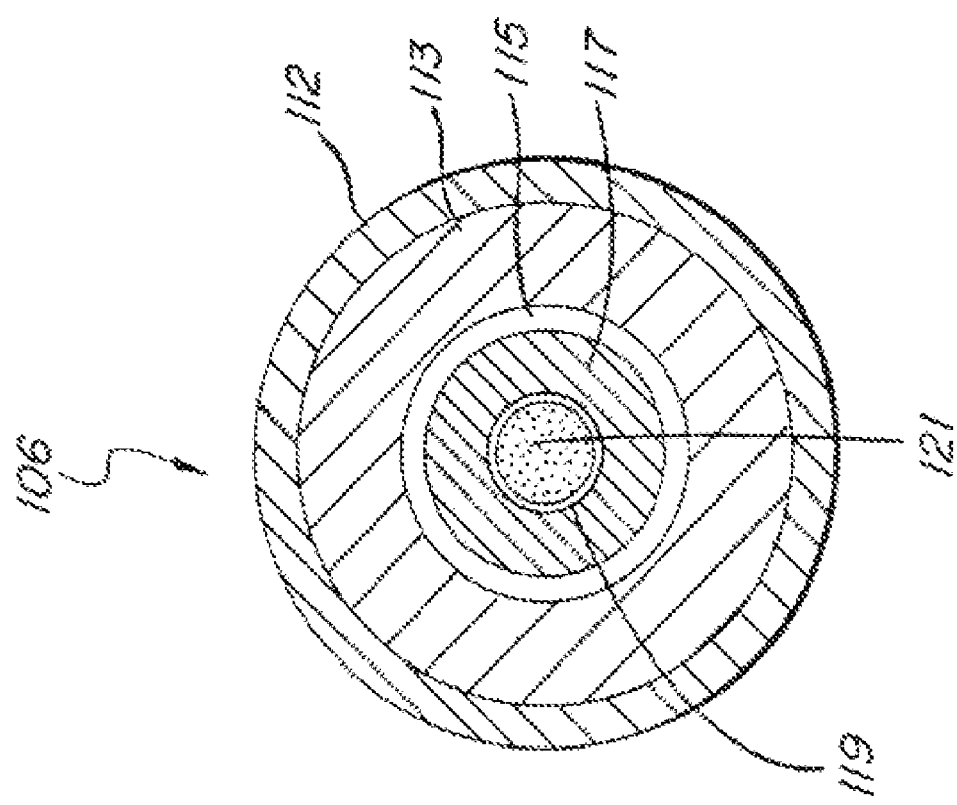
FIG. 7 is a cross sectional view of an electrolysis cell of an apparatus for measuring chlorine levels of the present disclosure.

FIG. 7 shows a cross-sectional view of the central cylindrical tube 106 of the electrolysis cell 103 (FIG. 6). Within the outer cylindrical tube 112, several components are concentrically disposed, including a outer graphite electrode 113, a ceramic separator tube 117, and an inner graphite electrode 121. The concentric arrangement of these components defines an outer slow chamber 115 and an inner flow chamber 119. Each of these components will now be described in detail. It will be appreciated that the embodiment described herein, including the dimensions described, are merely exemplary embodiments; equivalent structures or varying the dimensions are expressly contemplated.

Figure 8:
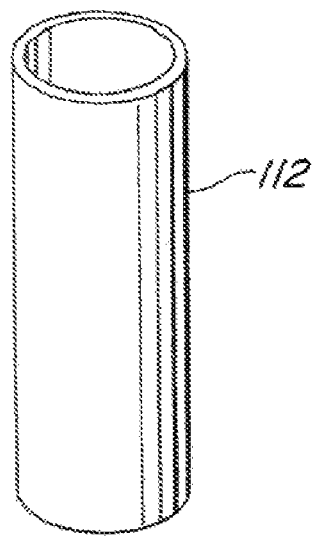
FIG. 8 is a perspective view of an embodiment of an outer cylindrical tube of an electrolysis cell.

FIG. 8 illustrates the outer cylindrical tube 112 of the electrolysis cell 103 in more detail. The outer cylindrical tube 112 may comprise a 1¼-inch grey standard PVC pipe, having, for example, an inside diameter of 28.60 mm and a length of 94.5 mm.

Figure 9:
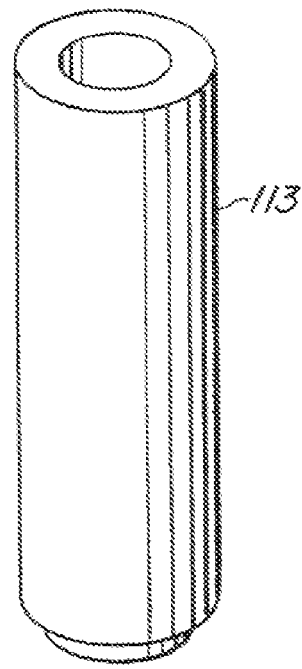
FIG. 9 is a perspective view of an embodiment of an outer graphite electrode of an electrolysis cell.

The outer graphite electrode 113 is illustrated further in FIG. 9. The outer graphite electrode 113 may have a length of 94.5 mm and an outside diameter of, for example, 28.50 mm so that it snugly mates with the outer cylindrical tube 112. The outer graphite electrode 113 further includes a cylindrical plug that fits within large inner cylindrical recess 123 (see FIG. 12) at an end thereof, around which an electrically conductive wire is wrapped, so that it is in intimate contact with the outer graphite electrode 113.

Figure 10:
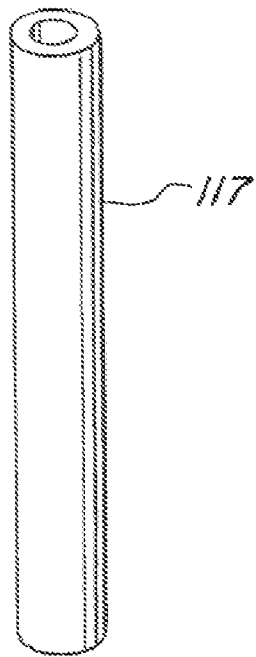
FIG. 10 is a perspective view of an embodiment of a ceramic separator tube of an electrolysis cell.

The ceramic separator tube 117 is illustrated in further detail in FIG. 10. It may have a length of, for example, of 100.50 mm, an inside diameter of 6.50 mm, and an outside diameter of 13.80 mm.

Figure 11:
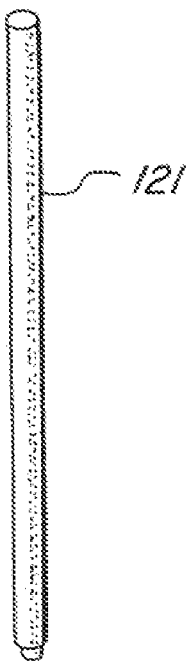
FIG. 11 is a perspective view of an embodiment of an inner graphite electrode of an electrolysis cell.

The inner graphite electrode 121 is illustrated in further detail in FIG. 11. It may have a length of 106.50 mm, an inner diameter of 3.5 mm, and an outer diameter of 5.0 mm.

Figure 12:
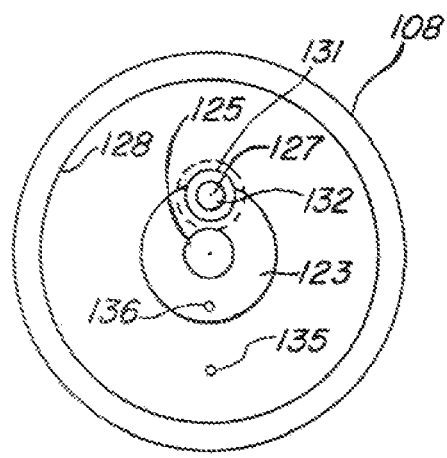
FIG. 12 is a top (interior) view of an embodiment of an electrolysis cell input end cap.
Figure 13:
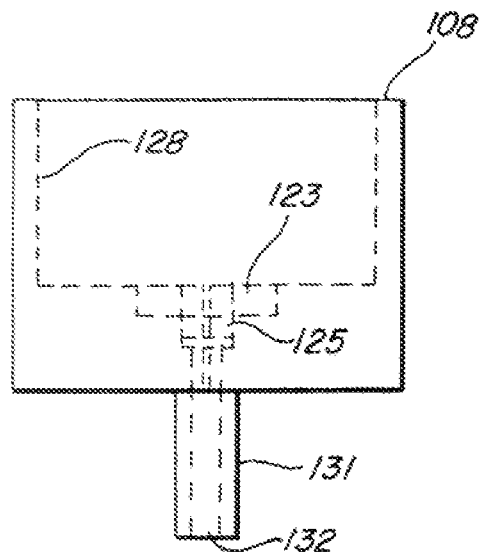
FIG. 13 is a side view of an embodiment of an electrolysis cell input end cap.
Figure 14:
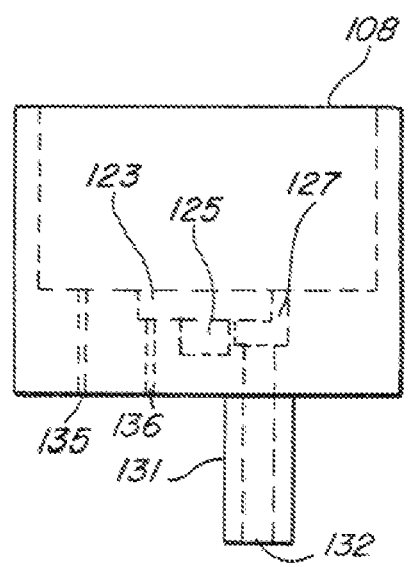
FIG. 14 is a side view of an embodiment of an electrolysis cell input end cap.

The electrolysis cell input end cap 108 is illustrated in further detail in FIGS. 12 through 14. As shown, the electrolysis cell input end cap 108 includes a sidewall 128, which snugly receives the outer cylindrical tube 112 of the electrolysis cell 103. According to embodiments, a large inner cylindrical recess 123 is shaped and dimensioned to snugly receive the ceramic separator tube 117 (See FIG. 7). Single input port 131, having a half-cell solution input conduit 132 ending at input well 127, allows the large inner cylindrical recess 123 to be in fluid communication with a half-cell solution source. As shown in FIG. 14, large inner cylindrical recess 123 positions ceramic separator tube 117 above the plane in which input well 127 opens. Therefore, as half-cell solution flows into input well 127 via half-cell solution input conduit 132, ceramic separator tube 117 divides the flow of half-cell solution entering into the electrolysis cell 103 into inner flow chamber 139 and outer flow chamber 115.

A small inner cylindrical recess 125 of lesser diameter than the large inner cylindrical recess 123 is concentrically disposed within the large inner cylindrical recess 123 and shaped and dimensioned to snugly receive the inner graphite electrode 121. Accordingly, each of outer cylindrical tube 112, ceramic separator 117, and inner graphite electrode 121 are registered in their proper orientation and position within the electrolysis cell 103. Two small apertures 135, 136 are further provided to for the electrical leads.

Figure 15:
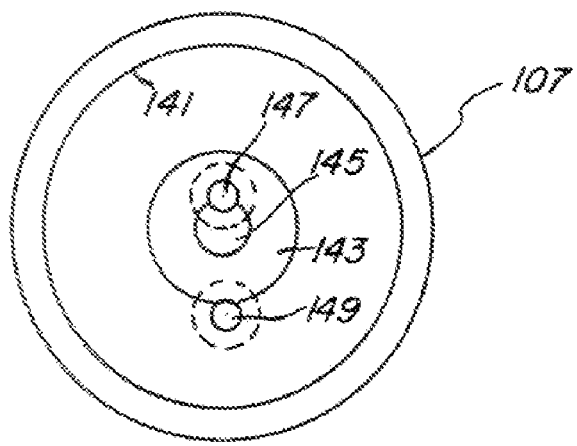
FIG. 15 is a top (interior) view of an embodiment of an electrolysis cell output end cap.
Figure 16:
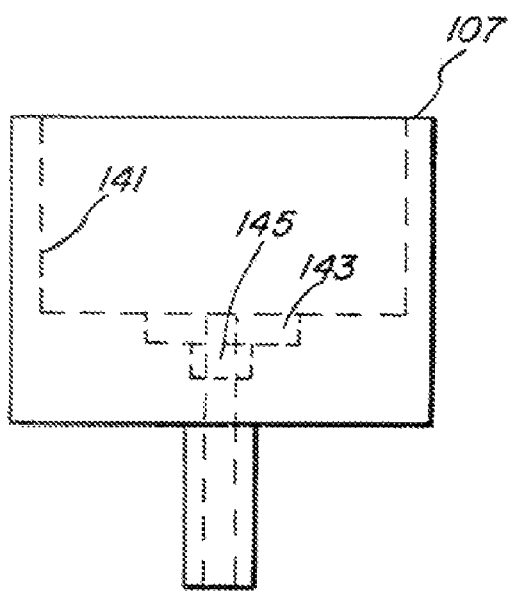
FIG. 16 is a side view of an embodiment of an electrolysis cell output end cap.
Figure 17:
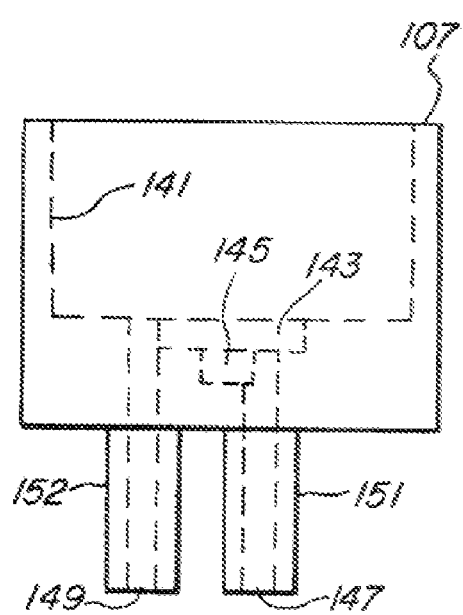
FIG. 17 is a side view of an embodiment of an electrolysis cell output end cap.

The electrolysis cell output end cap 107 is shown in further detail in FIGS. 15 through 17. The electrolysis cell output end cap 107 includes a recess 141 for snugly receiving the outer cylindrical tube 112. The electrolysis cell output end cap 107 also comprises concentric large outer cylindrical recess 143 and small outer cylindrical recess 145 for receiving and registering the ceramic separator tube 117 and the inner graphite electrode 121, respectively. Output channels 147, 149 are provided to provide outlets from the inner flow chamber 119 and outer flow chamber 115 through respective ports 151, 152.

Figure 18:
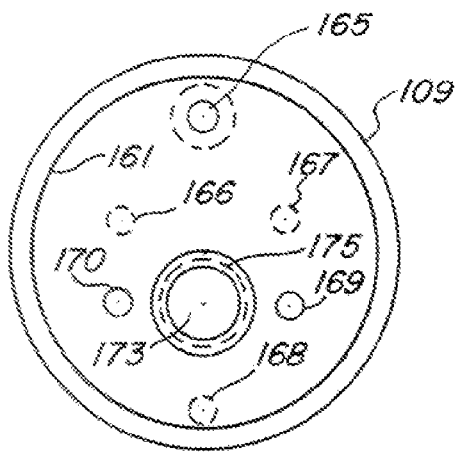
FIG. 18 is a top (interior) view of an embodiment of an optical cell end cap.
Figure 19:
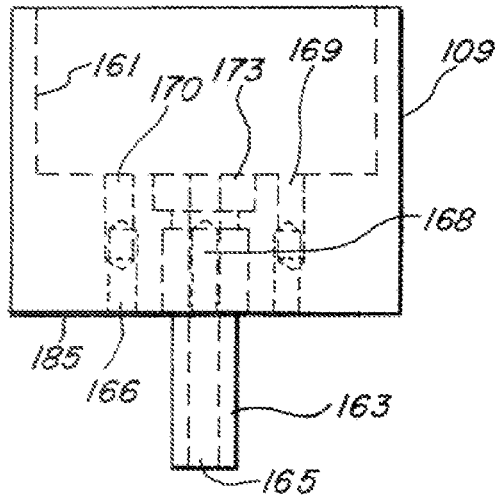
FIG. 19 is a side view of an embodiment of an optical cell end cap.
Figure 20:
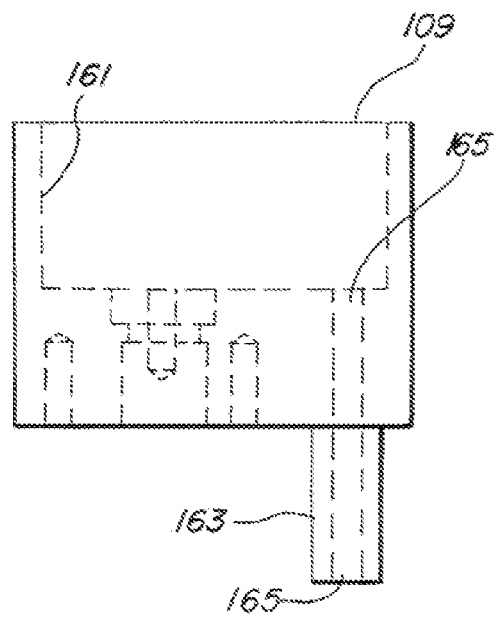
FIG. 20 is a side view of an embodiment of an optical cell end cap.

The optical end cap 109 of optical cell 105 is illustrated in FIGS. 18 through 20. As shown, the optical end cap 109 is generally cylindrical in shape and has an interior cylindrical wall 161 for mating with the outer cylindrical tube 212. Because of its symmetrical design, the end cap 109 can be used cm both the inlet and outlet ends of the optical cell 105.

The optical end cap 109 includes a fluid flow port 163 with conduit 165 placing the interior of the optical cell 105 into fluid communication with exterior components of the present disclosure. A cylindrical opening 175 is provided for mounting quartz window 173. The quartz window 173 and a cooperating O-ring seal are held in place via the optical cover member 179 of FIG. 21.

Figure 21:
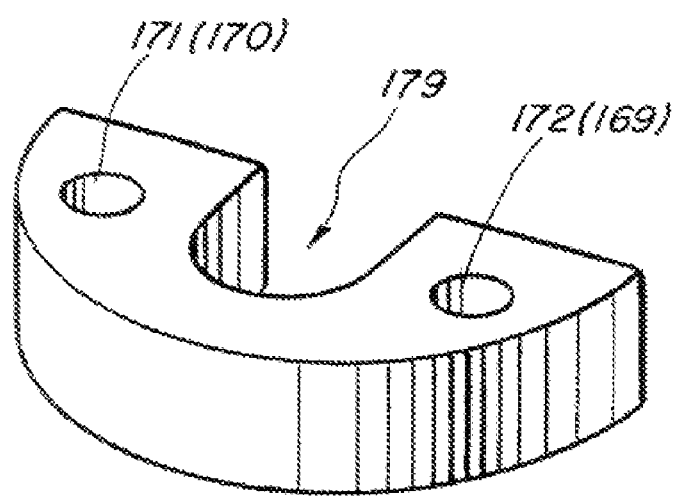
FIG. 21 is a perspective view of an embodiment of an optical cover member for holding a quartz window in place in an optical cell.

Referring still to FIG. 21, the optical cover member 179 contains cylindrical openings 172, 171 which register with tapped openings 169, 170 in the interior of the optical end cap 109. Fastening devices may then be inserted through the openings 171, 172 and threadably attached via tapped openings 169, 170 to securely seal the quarts window 173. As may be appreciated, the cylindrical opening 175 extends to the exterior end surface 185 of the end cap 109.

Figure 22:
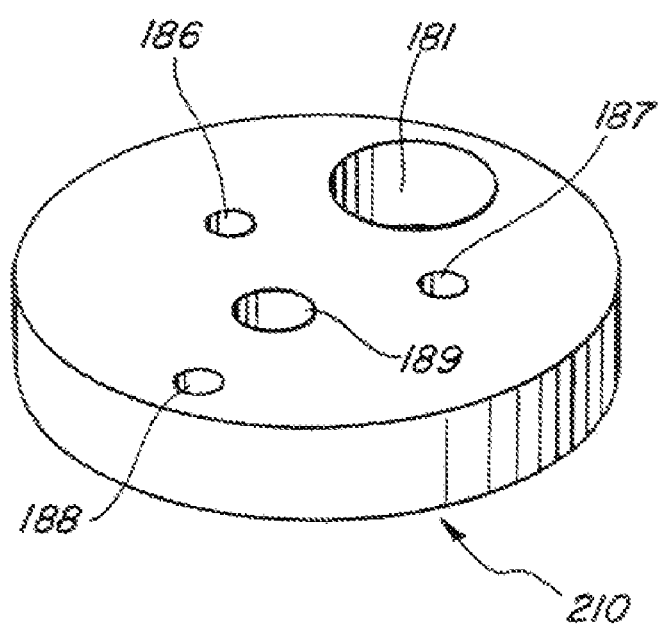
FIG. 22 is a perspective view of an embodiment of an end plate that attaches to an end cap of an optical cell.

Turning again to FIGS. 18 to 20, tapped openings 166, 167, 168 are also formed into the exterior of the optical end cap 109. These tapped openings permit attachment of the optical end plate 210 illustrated in FIG. 22. Openings 186, 187, 188 on optical end plate 210 register with the openings 166, 167, 168 on the optical end cap 109 to permit attachment of the end plate 210 to optical end cap 109.

The end plate 210 further includes a cylindrical opening 181, which at the input end of the optical cell 105 mounts a UV source 213 (see FIG. 23), which is a UV LED according to an embodiment. On the output end of the optical cell 105, an optical end plate 210 mounts and retains a photo detector 215, functioning as a UV detector. Thus, in operation, a UV source 213 retained at the input end of the optical cell 105 directs UV illumination through the solution contained within the central cylindrical tube 212, which is then detected by the photo detector 215 mounted in the output end cap 109. A cylindrical opening 189 facilitates cable strain relief/attachment and passage of suitable electrical cables.

Figure 23:
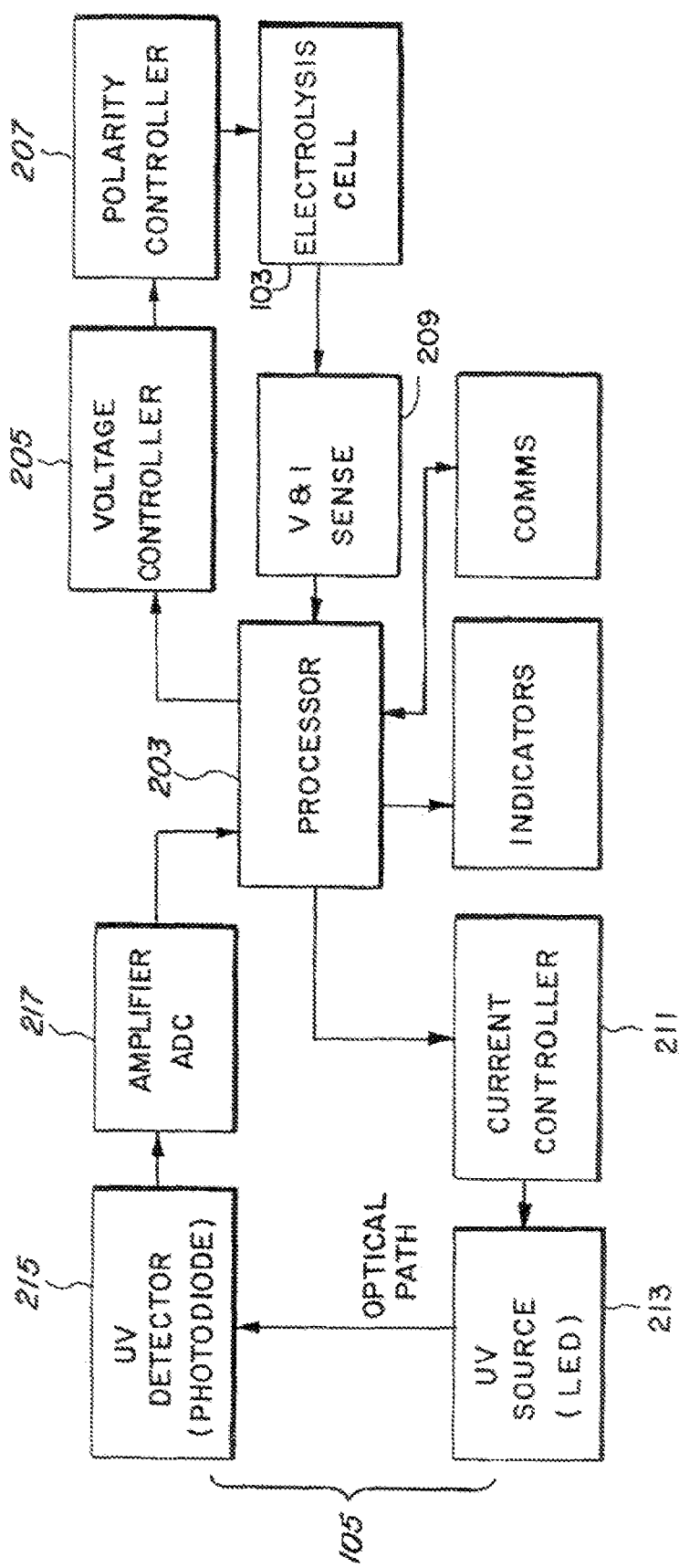
FIG. 23 is a block diagram of an embodiment of electronic control circuitry that controls an apparatus for measuring chlorine dioxide levels.

The electronic control circuitry for tire system shown in FIG. 23 is configured around processor 203, which may be, for example, an eight-bit microcontroller. With respect to the electrolysis cell 103, the processor 203 controls the voltage across the cell 103 via voltage controller 205, which outputs to a polarity controller 207. The polarity controller 207 in an illustrative embodiment may be an H bridge, which permits both positive and negative driving polarities to be applied to the electrolysis cell 103.

The voltage across and current through the electrolysis cell 103 is sensed by a current and voltage sensing apparatus 209 and signals representative of those respective quantities are supplied to the processor 203. The voltage and current measurements are measurements that allow the processor 203 to detect both normal and abnormal operation of the system. At a low voltage, the conductivity of the solution may be determined, which is a parameter related to the level of soluble salts in the spa water solution. Abnormally high conductivity may be used to indicate that the water needs to be replaced with clean water. An abnormally low conductivity may indicate that there is no water present in the sensors, and that the spa is empty, or some other fault is present that requires intervention to correct. The processor 203 may then indicate a fault condition by illuminating a 'fault' light. During normal operation, the processor 203 uses the conductivity reading to drive the electrolysis cell 103 with a constant current, by applying a variable voltage. This ensures that a constant change in pH is obtained, independent to a variable solution conductivity.

With respect to the optical cell 105, the processor 203 controls the current level supplied to the UV source 213 from a constant current supply 211. The UV source 213 may be a UVTOP LED as available from Sensor Electronic Technology, Inc., 1195 Atlas Road, Columbia, S.C. 29209. The photo detector 215 develops a signal representative of the transmitted UV light and supplies that signal to an amplifier/analog to digital converter 217 (ADC). The output of the amplifier/ADC 217 is then supplied to the processor 203 which performs those computations necessary to determine the chlorine level.

In one embodiment, the processor 203 takes three UV absorption readings and uses these values to determine the hypochlorite level. The first reference reading, R1, is of the spa solution when no pH shift has taken place, the second, R2, when a positive shift has taken place and the third, R3, after a negative shift has taken place. The shift readings are normalized, by dividing them by the first reference reading. The difference between the two normalized shift readings is taken, and the answer logged. The result, X, is a value that is directly proportional to the free hypochlorite level. The exact level of hypochlorite can be determined by calculation, using X to complete the only unknown in a linear equation of the form Y=MX+C, where M and C are constants previously found by calibration and Y is the level of tree hypochlorite in parts-per-million.

$$X = \text{Log}\ [(R2/R1) - (R3/R1)] \qquad \text{Equation (1)}$$

$$Y = MX + C \qquad \text{Equation (2)}$$

Thus, combining (1) and (2), the equation relating free chlorine to measurements is:

$$Y = M(\text{Log}\ [(R2/R1) - (R3/R1)]) + C \qquad \text{Equation (3)}$$

If processing power is a limited resource, but sufficient memory is available in the processor 203, then an alternative method can be used to determine the free chlorine level. In this method, an intermediate value is found, so as to avoid the logarithmic calculation, which is computationally expensive on low cost microprocessors. The value D is obtained by normalizing and differencing the sensor readings. The value of Y, the level of free hypochlorite, is found by searching down a look-up table of values of D until a matching entry is found at index I. The free chlorine level can then be read out of the table, by examining its entry located at index I.

$$D = (R2/R1) - (R3/R1) \qquad \text{Equation (4)}$$

$$N(I) = D, \text{ to find } I \qquad \text{Equation (5)}$$

$$Y = Y(I)$$

According to an embodiment, the basic commands for the processor 203 are relatively simple:

a. take a reading ("s" command)
b. take a current reading ("i" command)
c. take a voltage reading ("v" command)
d. set the electrolysis cell drive level ("e, [number]").

Figure 24:
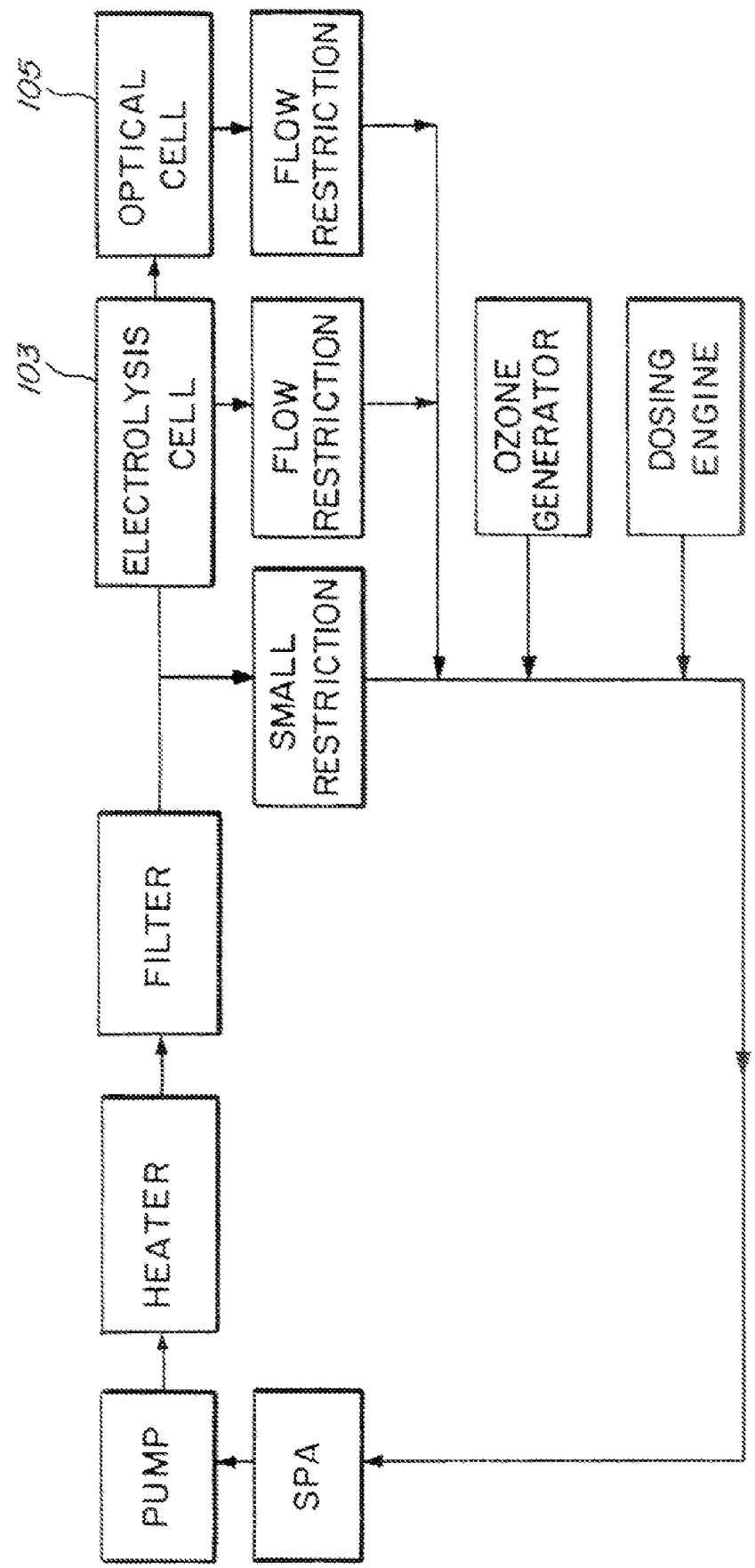
FIG. 24 is a block diagram of an embodiment a plumbing system employing the apparatus for measuring chlorine levels.

A plumbing schematic for an illustrative embodiment is shown in FIG. 24. As shown, a conventional spa pump, heater, and filter circuit supplies spa water at a relatively low flow rate to the electrolysis cell 103, which outputs to the optical cell 105. Both the optical cell 105 and electrolysis cell 103 output to respective flow restrictors, and both flow restrictors connect to the return line to the spa. A small restriction from the filter to the return is used to draw most of the pump pressure, thereby permitting a relatively low flow rate at the entrance to the electrolysis cell 103.

With respect to design considerations, it is desirable to avoid very low flow rates. It is further desirable to ensure a stable flow of water running through both paths and to further ensure that the entry and exit fluid streams are at the same temperature as the spa.

In operation of the system, a number of pH readings are taken. An "s" command is sent to the electronic controller, and then, over a period of 250 milliseconds, the unit takes sixteen readings and returns an answer in the format "s, [number]" to the processor 203.

Next the pH is changed. This change is accomplished by sending a command "e, [number]" to the H bridge, after which the voltage and polarity across the electrolysis cell 103 are set. UV transmission data is then taken and examined by the processor 203 to ascertain when the pH of the solution in the optical cell 105 stabilized, which may take many minutes.

It is further desirable to confirm that a valid pH change has occurred, either by measuring the pH directly or by calculating it based on a known flow rate, V drive, I drive, and the water conductivity measured at a low V drive.

Once valid absorption data has been taken, an "overdrive" method may be used if desired to calculate free chlorine. In this method, readings are taken at both high and low pH levels, and the difference between the two sensor measurements is determined. The logarithm of this difference value may then be taken to find the absorbance, which is proportional to free chlorine. The exact chlorine level value may be determined by using a linear formula based on a calibration curve.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and What is clamed is:

1. A method of measuring the level of a substance in a first solution comprising:
    changing the pH of a first sample of the first solution to a first selected value, thereby producing a first pH adjusted sample;
    performing a first measurement of electromagnetic radiation transmissivity of the first pH adjusted sample;
    changing the pH of a second sample of the first solution to a second selected value, thereby producing a second pH adjusted sample;
    performing a second measurement of the electromagnetic radiation transmissivity of the second pH adjusted sample; and
    determining the level of the substance using the result of each of the first and second measurements.

2. The method of claim 1, wherein the transmissivity of each of the first pH adjusted sample and the second pH adjusted sample is determined at the same wavelength of electromagnetic radiation.

3. The method of claim 2, wherein the wavelength is 293 nanometers.

4. The method of claim 1, wherein the solution comprises pool or spa tub water.

5. The method of claim 4, wherein the substance is a halogen.

6. The method of claim 5, wherein the substance is chlorine or bromine.

7. The method of claim 1, wherein the solution comprises water that is intended to be potable.

8. The method of claim 1, wherein the step of determining comprises determining a difference value between the light transmissivity measured by the first measurement and the light transmissivity measured by the second measurement.

9. The method of claim 8, wherein the step of determining further comprises comparing the difference value to a table comprising a range of substance levels and a pre-determined difference value corresponding to each level in the range.

10. The method of claim 1, wherein the step of determining comprises using the result of the first and second measurements in a logarithmic calculation.

11. The method of claim 1, wherein the pH of the first pH adjusted solution is at a first level of acidity and the pH of the second pH adjusted solution is at a second level of acidity.

12. The method of claim 1, wherein the first pH adjusted solution is produced by applying a first voltage of a first polarity to the first sample.

13. The method of claim 12, wherein the second pH adjusted solution is produced by applying a second voltage of polarity opposite to the polarity of said first voltage to the second sample.

14. The method of claim 13, wherein the same liquid containing vessel is used to produce the first and second pH adjusted samples.

15. A method of measuring the level of a substance in a first solution comprising:
    applying a first electrical voltage to change the pH of a first sample of the first solution to a first value, thereby producing a first pH adjusted sample;
    performing a first measurement of electromagnetic radiation transmissivity of the first pH adjusted sample;
    applying a second electrical voltage to change the pH of a second sample of the first solution to a second value, thereby producing a second pH adjusted sample;
    performing a second measurement of the electromagnetic radiation transmissivity of the second pH adjusted sample; and
    determining the level of the substance in the first solution using the result of each of the first and second measurements.

16. The method of claim 15, wherein the transmissivity of each of the first pH adjusted sample and the second pH adjusted sample is determined at the same wavelength of electromagnetic radiation.

17. The method of claim 16, wherein the wavelength is 293 nanometers.

18. The method of claim 15, wherein the solution comprises pool or spa tub water.

19. The method of claim 18, wherein the substance is a halogen.

20. The method of claim 19, wherein the substance is chlorine or bromine.

21. The method of claim 15, wherein said first measurement and second measurement each comprise a measurement of ultraviolet (UV) light transmissivity.

22. The method of claim 21, wherein said first and second measurements are made at the same UV wavelength.

23. The method of claim 15, wherein the step of determining comprises determining a difference value between the light transmissivity measured by the first measurement and the light transmissivity measured by the second measurement wherein the level of the substance being measured is a function of said difference value.

24. The method of claim 23, wherein the step of determining further comprises comparing the difference value to a table comprising a range of substance levels and a pre-determined difference value corresponding to each level in the range.

25. The method of claim 23, wherein the step of determining comprises taking a logarithm of the difference value.

26. A method of measuring the level of a substance in a first solution having a first chemical composition comprising:
    applying a first electrical voltage to change the pH of a first sample of the first solution, thereby producing a first pH adjusted sample, the first pH adjusted sample having a second chemical composition different from said first chemical composition;
    performing a first measurement of electromagnetic radiation transmissivity of the first pH adjusted sample;
    applying a second electrical voltage to change the pH of a second sample of the first solution, thereby producing a second pH adjusted sample, the second pH adjusted sample having a third chemical composition different from said first and second chemical compositions;
    performing a second measurement of the electromagnetic radiation transmissivity of the second pH adjusted sample;
    employing said first and second measurements to determine the level of the substance in the first solution.

27. The method of claim 26, wherein the transmissivity of each of the first pH adjusted sample and the second pH adjusted sample is determined at the same wavelength of electromagnetic radiation.

28. The method of claim 27, wherein the wavelength is 293 nanometers.

29. The method of claim 26, wherein the solution comprises pool or spa tub water.

30. The method of claim 26, wherein the substance is a halogen.

31. The method of claim 30, wherein the substance is chlorine or bromine.

32. The method of claim 26, wherein said first measurement and second measurement each comprise a measurement of ultraviolet (UV) light transmissivity.

33. The method of claim 26, wherein a programmed computer processor employs said first and second measurements as variables to compute the level of said substance in said solution.

34. The method of claim 26, wherein the step of determining comprises determining a difference value between the light transmissivity measured by the first measurement and the light transmissivity measured by the second measurement wherein the level of the substance being measured is a function of said difference value.

35. The method of claim 34, wherein the step of determining further comprises comparing the difference value to a table comprising a range of substance levels and a pre-determined difference value corresponding to each level in the range.

36. The method of claim 26, wherein the step of determining comprises using the result of the first and second measurements in a logarithmic calculation.

* * * * *